(12) United States Patent
Plos

(10) Patent No.: US 6,582,477 B1
(45) Date of Patent: Jun. 24, 2003

(54) OXIDATION DYEING PROCESS USING A KETOSE AS REDUCING AGENT AND A LACCASE AS OXIDIZING AGENT

(75) Inventor: Grégory Plos, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/545,683

(22) Filed: Apr. 6, 2000

(30) Foreign Application Priority Data

Apr. 7, 1999 (FR) .............................................. 99 04338

(51) Int. Cl.$^7$ ................................................. A61K 7/13
(52) U.S. Cl. ........................ 8/405; 8/406; 8/407; 8/410; 8/411; 8/412; 8/426
(58) Field of Search ............................ 8/405, 406, 407, 8/410, 411, 412, 426

(56) References Cited

U.S. PATENT DOCUMENTS

| | | | |
|---|---|---|---|
| 3,251,742 A | 5/1966 | Soloway | 167/88 |
| 4,003,699 A | 1/1977 | Rose et al. | 8/10.2 |
| 4,217,914 A | 8/1980 | Jacquet et al. | 132/7 |
| 4,823,985 A | 4/1989 | Grollier et al. | 222/1 |
| 4,842,849 A * | 6/1989 | Grollier et al. | 424/70 |
| 5,061,289 A | 10/1991 | Clausen et al. | 8/405 |
| 5,380,340 A | 1/1995 | Neunhoeffer et al. | 8/409 |
| 5,534,267 A | 7/1996 | Neunhoeffer et al. | 424/701 |
| 5,663,366 A | 9/1997 | Neunhoeffer et al. | 548/371.4 |
| 5,735,908 A | 4/1998 | Cotteret et al. | 8/410 |
| 6,093,221 A | 7/2000 | Grüll et al. | 8/579 |
| 6,106,579 A * | 8/2000 | Kunz et al. | 8/432 |

FOREIGN PATENT DOCUMENTS

| | | | |
|---|---|---|---|
| DE | 23 59 399 | 6/1975 | |
| DE | 38 43 892 | 6/1990 | |
| DE | 41 33 957 | 4/1993 | |
| EP | 0 504 005 | 9/1992 | |
| EP | 0 673 641 | 9/1995 | |
| FR | 2 112 549 | 6/1972 | |
| FR | 2 270 846 | 12/1975 | |
| FR | 2 586 913 | 3/1987 | |
| FR | 2 694 018 | 1/1994 | |
| GB | 1 026 978 | 4/1966 | |
| GB | 1 153 196 | 5/1969 | |
| WO | WO 94/08969 | 4/1994 | |
| WO | WO 94 08970 | 4/1994 | |
| WO | WO 95/07988 | 3/1995 | |
| WO | WO 95/33836 | 12/1995 | |
| WO | WO 95/33837 | 12/1995 | |
| WO | WO 96/00290 | 1/1996 | |
| WO | WO 97/19998 | 6/1997 | |
| WO | WO 97/19999 | 6/1997 | |
| WO | WO 98/24967 | 6/1998 | |
| WO | WO 98/40471 | * 9/1998 | C12N/9/02 |

OTHER PUBLICATIONS

English language Derwent Abstract of EP 0 504 005.
English language Derwent Abstract of FR 2 112 549.
English language Derwent Abstract of FR 2 694 018.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, LLP

(57) ABSTRACT

The present invention relates to dyeing compositions containing, in a medium appropriate for dyeing, at least one oxidation dye precursor and/or one or more couplers, a ketose as reducing agent and at least one laccase as oxidizing agent, to the use of the compositions for the oxidation dyeing of keratin fibers, and in particular human keratin fibers such as the hair, to dyeing processes using the compositions, and to dyeing kits using the compositions.

69 Claims, No Drawings

OXIDATION DYEING PROCESS USING A KETOSE AS REDUCING AGENT AND A LACCASE AS OXIDIZING AGENT

The present invention relates to dyeing compositions comprising, in a medium appropriate for dyeing, at least one oxidation dye precursor and/or one or more couplers, a ketose as reducing agent and at least one laccase as oxidizing agent, to the use of the compositions for the oxidation dyeing of keratin fibers, and in particular human keratin fibers such as the hair, to dyeing processes using the compositions, and to dyeing devices using the compositions.

It is known to dye keratinous fibers, and in particular the hair, with dyeing compositions comprising oxidation dye precursors generally known as "oxidation bases," in particular ortho- or para-phenylenediamines, ortho- or para-aminophenols and heterocyclic bases.

Oxidation dye precursors are compounds, initially colorless or only slightly colored, which develop their dyeing power within the individual hair in the presence of an oxidizing agent. The oxidizing agent used is generally hydrogen peroxide. The formation of the colored compounds results either from a condensation of the "oxidation bases" with themselves or from a condensation of the "oxidation bases" with coloring-modifying compounds or "couplers," which are generally present in the dyeing compositions used in oxidation dyeing and which are represented more particularly by meta-phenylenediamines, meta-aminophenols, meta-diphenols and some heterocyclic compounds.

The variety of the molecules involved, which are composed, on the one hand, of the "oxidation bases" and, on the other hand, of the "couplers," makes it possible to obtain a rich palette of colors.

The oxidation coloring of keratinous fibers can also be carried out using different oxidizing systems than hydrogen peroxide systems, such as enzymatic systems. For example, it is known in U.S. Pat. No. 3,251,742 and Patent Applications FR-A-2 112 549, FR-A-2,694,018, EP-A-0,504,005, WO 95/07988, WO 95/33836, WO 95/33837, WO 96/00290, WO 97/19998 and WO 97/19999, the disclosures of which are incorporated by reference herein, to dye keratinous fibers with compositions comprising at least one oxidation dye in combination with enzymes of the laccase type, these compositions being brought into contact with atmospheric oxygen. These enzyme systems are advantageous because it has been observed that aqueous hydrogen peroxide solution can result in damage to the hair fiber and, in addition, in partial attack on the melanin of the hair, which results in the fiber becoming lighter in color.

It has also been found that, in some cases, laccases make it possible to obtain satisfactory oxidation colorings by using only couplers, without oxidation bases. Thus, in the present invention, the term "oxidation dye" covers oxidation dye precursors and/or couplers.

In order to be able to preserve oxidation dyes, i.e., oxidation dye precursors and/or couplers, it is necessary to combine them with a reducing agent. However, the inventor has found that these reducing agents generally slow down the absorption of the dyes on the fibers, which is reflected by less luminous shades and less intense colorings. In order to obtain an equivalent chromaticity, it is then necessary to use larger amounts of dyes.

Furthermore, numerous reducing agents used until now have an inhibiting effect on the activity of laccase.

After much research carried out in this field, the inventor has just discovered that the use of a ketose as reducing agent when a laccase is used as oxidizing agent makes it possible to solve the above-mentioned problems. This is because it has been found that ketoses do not inhibit the activity of laccase. It has also been found, surprisingly, that the mixture thus produced does not slow down the absorption of the oxidation dyes on the hairs.

Furthermore, these compositions give rise to more chromatic (more luminous) shades and to more intense colorings in comparison with equivalent compositions comprising conventional reducing agents and oxidizing agents. The colorings obtained also exhibit good resistance to perspiration, to light and to shampoos.

The invention also makes it possible to decrease the amount of coloring active materials used in dyeing compositions, in comparison with conventional techniques known in the prior art.

A subject of the present invention is thus the use of a ketose as reducing agent, in an amount ranging from 0.1 to 15% by weight with respect to the total weight of the composition, and of a laccase as oxidizing agent in oxidative dyeing.

Another subject of the invention relates to a process for dyeing keratinous fibers and in particular human keratinous fibers, such as the hair, which comprises:
  applying, to the fibers, a dyeing composition (A) comprising, in a medium appropriate for dyeing, at least one oxidation dye and a ketose as reducing agent, in an amount ranging from 0.1 to 15% by weight with respect to the total weight of the composition (A), and
  developing the color, in the presence of air, in an alkaline, neutral or acidic medium, using a laccase as oxidizing agent, the laccase either being incorporated in the composition (A), in which case the composition (A) is stored with air excluded, or in a composition (B), in which case the compositions (A) and (B) are mixed immediately before use or applied one after the other to the keratinous fibers.

The oxidation dye is preferably an oxidation dye precursor with optionally one or more couplers.

The oxidation dye can also be composed of one or more couplers, i.e., without oxidation dye precursors.

In a preferred form of the invention, the ketose is present in proportions ranging from 5 to 10% with respect to the total weight of the composition (A).

The ketoses according to the present invention are in particular $C_3$–$C_8$ ketoses, and preferably $C_6$ ketoses (ketohexoses).

In particular, mention may be made, as examples of ketoses, of xylulose, ribulose, fructose, sedoheptulose, tagatose, sorbose and psicose. Their optical isomers (or enantiomers) in the D or L form can be used in the present invention, whether in the pure form (D or L) or in the paired form (D and L).

Fructose (D and/or L form) is particularly preferred.

The laccase or laccases used in the process according to the invention can be chosen in particular from laccases of plant origin, animal origin, fungal origin (yeasts, moulds or mushrooms) and bacterial origin, it being possible for the source organisms to be mono- or multicellular. The laccase or laccases can also be obtained by biotechnology.

Mention may be made, among the laccases of plant origin which can be used according to the invention, of the laccases produced by plants carrying out chlorophyll synthesis, as indicated in Application FR-A-2,694,018, the disclosure of which is incorporated by reference herein, such as those which are found in extracts of the Anacardiaceae, such as, for example, extracts of *Magnifera indica, Schinus molle* and *Pleiogynium timoriense*, and in extracts of the *Podocarpaceae, Rosmarinus* off., *Solanum tuberosum, Iris* sp., *Coffea* sp., *Daucus carrota, Vinca minor, Persea americana, Catharenthus roseus,* Musa sp., *Malus pumila, Gingko biloba, Monotropa hypopithys* (Indian pipe), Aesculus sp., *Acer pseudoplatanus, Prunus persica* and *Pistacia palaestina*.

Mention may be made, among the laccases of fungal origin optionally obtained by biotechnology which can be used according to the invention, of the laccase or laccases resulting from Polyporus versicolor, *Rhizoctonia praticola* and *Rhus vernicifera*, as indicated in Applications FR-A-2, 112,549 and EP-A-504,005, the disclosures of which are incorporated by reference herein, and those laccases disclosed in Patent Applications WO 95/07988, WO 95/33836, WO 95/33837, WO 96/00290, WO 97/19998 and WO 97/19999, the contents of which form an integral part of the present description and the disclosures of which are incorporated by reference herein, such as, for example, those resulting from Scytalidium, *Polyporus pinsitus, Myceliophtora thermophila, Rhizoctonia solani, Pyricularia orizae,* and their variants. Mention may also be made of those laccases resulting from *Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens*, and their variants.

Laccases of fungal origin optionally obtained by biotechnology are particularly preferred.

The enzymatic activity of the laccases of the invention having syringaldazine among their substrates can be defined from the oxidation of syringaldazine under aerobic conditions. The lacu unit corresponds to the amount of enzyme catalysing the conversion of 1 mmol of syringaldazine per minute at pH 5.5 and at 30° C. The u unit corresponds to the amount of enzyme producing a delta of absorbance at 530 nm of 0.001 per minute using syringaldazine as substrate, at 30° C. and at pH 6.5.

The enzymatic activity of the laccases of the invention can also be defined from the oxidation of para-phenylenediamine. The ulac unit corresponds to the amount of enzyme producing a delta of absorbance at 496.5 nm of 0.001 per minute using para-phenylenediamine as substrate (64 mM), at 30° C. and at pH 5.

The amounts of laccase used in the compositions of the invention will vary according to the nature of the laccase chosen. They will preferably vary from 0.5 to 3000 lacu or from 1000 to $6 \times 10^7$ u units or from 20 to $3 \times 10^6$ ulac units per 100 g of composition applied to the hair.

The oxidation dyes which can be used in the context of the present invention are chosen from those conventionally known in oxidation dyeing.

Mention may particularly be made of the following oxidation dye precursors:

the para-phenylenediamines of following formula (I) and the acid addition salts of these compounds:

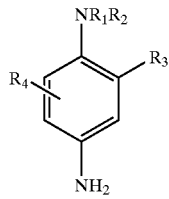

(I)

in which
R$_1$ represents a hydrogen atom or a C$_{1-4}$ alkyl, C$_{1-4}$ monohydroxyalkyl, C$_{2-4}$ polyhydroxyalkyl or 4'-aminophenyl radical,
R$_2$ represents a hydrogen atom or a C$_{1-4}$ alkyl, C$_{1-4}$ monohydroxyalkyl or C$_{2-4}$ polyhydroxyalkyl radical,
R$_3$ represents a hydrogen atom, a halogen atom, such as a chlorine atom, or a C$_{1-4}$ alkyl, sulfo, carboxyl, C$_{1-4}$ monohydroxyalkyl or C$_{1-4}$ hydroxyalkoxy radical, and
R$_4$ represents a hydrogen atom or a C$_{1-4}$ alkyl radical.

Mention may particularly be made, among the para-phenylenediamines of formula (I) above, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine and the acid addition salts of these compounds.

Among the para-phenylenediamines of formula (I), para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and the acid addition salts of these compounds are particularly preferred.

Mention may also be made of the following oxidation dye precursors:

the bisphenylalkylenediamines of formula (II) and the acid addition salts of these compounds:

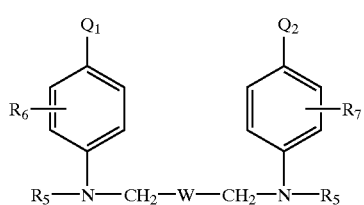

(II)

in which

Q$_1$ and Q$_2$, which are identical or different, represent a hydroxyl radical or an NHR$_8$ radical in which R$_8$ represents a hydrogen atom or a C$_{1-4}$ alkyl radical, R$_5$ represents a hydrogen atom or a C$_{1-4}$ alkyl, C$_{1-4}$ monohydroxyalkyl, C$_{2-4}$ polyhydroxyalkyl or C$_{1-4}$ aminoalkyl radical, it being possible for the amino group to be substituted, R$_6$ and R$_7$, which are identical or different, represent a hydrogen or halogen atom or a C$_{1-4}$ alkyl radical, and W represents a radical chosen from the group formed by the following radicals:

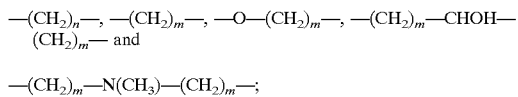

in which n is an integer ranging from 0 to 8, and m is an integer ranging from 0 to 4.

Mention may particularly be made, among the bisphenylalkylenediamines of formula (II) above, of N,N'-bis(β-hydroxyethyl)-N,N'-bis(4-aminophenyl)-1,3-diamino-2-propanol, N,N'-bis(β-hydroxyethyl)-N,N'-bis(4-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(β-hydroxyethyl)-N,N'-bis(4-aminophenyl)tetramethylenediamine, N,N'-diethyl-N,N'-bis(4-amino-3-methyl-phenyl)ethylenediamine and the acid addition salts of these compounds.

Among these bisphenylalkylenediamines of formula (II), N,N'-bis(β-hydroxyethyl)-N,N'-bis(4'-aminophenyl)-1,3-diamino-2-propanol or one of its addition salts with an acid is particularly recommended.

Mention may also be made of the following oxidation dye precursors:

the para-aminophenols corresponding to the formula (III) and the acid addition salts of these compounds:

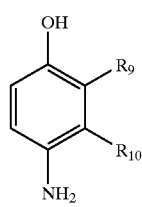

(III)

in which

R$_9$ represents a hydrogen atom or a C$_{1-4}$ alkyl, C$_{1-4}$ monohydroxyalkyl, (C$_{1-4}$ alkoxy)(C$_{1-4}$ alkyl), C$_{1-4}$ aminoalkyl or hydroxy(C$_{1-4}$ alkyl)amino(C$_{1-4}$ alkyl) radical, and R$_{10}$ represents a hydrogen or fluorine atom or a C$_{1-4}$ alkyl, C$_{1-4}$ monohydroxyalkyl, C$_{2-4}$ polyhydroxyalkyl, C$_{1-4}$ aminoalkyl, cyano(C$_{1-4}$ alkyl) or (C$_{1-4}$ alkoxy)(C$_{1-4}$ alkyl) radical, with the proviso that at least one of the R$_9$ or R$_{10}$ radicals represents a hydrogen atom.

Mention may particularly be made, among the para-aminophenols of formula (III) above, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol, and the acid addition salts of these compounds.

The ortho-aminophenols which can be used as oxidation bases in the context of the present invention are chosen in particular from 2-aminophenol, 2-amino-1-hydroxy-5-methylbenzene, 2-amino-1-hydroxy-6-methylbenzene, 5-acetamido-2-aminophenol and the acid addition salts of these compounds.

The heterocyclic bases which can be used as oxidation bases in the context of the present invention are chosen in particular from pyridine derivatives, pyrimidine derivatives, pyrazole derivatives and the acid addition salts of these compounds.

Mention may more particularly be made, among the pyridine derivatives, of the compounds disclosed, for example, in Patents GB-1,026,978 and GB-1,153,196, the disclosures of which are incorporated by reference herein, such as 2,5-diaminopyridine, and the acid addition salts of such compounds.

Mention may particularly be made, among the pyrimidine derivatives, of the compounds disclosed, for example, in German Patent DE-2,359,399 or Japanese Patents JP-88-169,571, the disclosures of which are incorporated by reference herein, such as 2,4,5,6-tetraaminopyrimidine or 4-hydroxy-2,5,6-triaminopyrimidine, and the acid addition salts of such compounds.

Mention may more particularly be made, among the pyrazole derivatives, of the compounds disclosed in Patents DE-3,843,892 and DE-4,133,957 and Patent Applications WO-94/08969 and WO 94/08970, the disclosures of which are incorporated by reference herein, such as 4,5-diamino-1-methylpyrazole, 3,4-diaminopyrazole or 4,5-diamino-1-(4'-chlorobenzyl)pyrazole, and the acid addition salts of these compounds.

According to the invention, the oxidation dye precursor or precursors preferably represent from 0.0005 to 12% by weight of the total weight of the composition (A), and more preferably from 0.005 to 6% by weight approximately.

The couplers which can be used in the dyeing process according to the invention are those conventionally used in oxidation dyeing compositions, such as, for example, meta-phenylenediamines, meta-aminophenols and meta-diphenols (resorcinols), mono- or polyhydroxylated naphthalene derivatives, sesamol and its derivatives, and heterocyclic compounds, such as, for example, indole couplers, indoline couplers or pyridine couplers, and the acid addition salts of such compounds.

These couplers can be chosen in particular from 2-methyl-5-aminophenol, 5-N-(β-hydroxyethyl)-amino-2-methylphenol, 3-aminophenol, 1,3-dihydroxybenzene, 1,3-dihydroxy-2-methylbenzene, 4-chloro-1,3-dihydroxybenzene, 1-(β-hydroxyethoxy)-2,4-diaminobenzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one and the acid addition salts of such compounds.

When they are present, these couplers preferably represent from approximately 0.0001 to 10% by weight of the total weight of the composition (A), and in particular from approximately 0.005 to 5% by weight.

The acid addition salts of the chromogenic compounds, namely the oxidation bases and the couplers, are chosen in particular from hydrochlorides, hydrobromides, sulphates, tartrates, lactates and acetates.

In addition to the oxidation dyes defined above, the composition (A) can comprise direct dyes for enriching the shades with highlights. These direct dyes can be chosen in particular from nitro, azo or anthraquinone dyes.

The composition (A) and/or the composition (B) can additionally comprise at least one amphoteric or cationic substantive polymer, such as those defined in EP-A-0,673, 641, the disclosure of which is incorporated by reference herein, among which it is preferable to employ:

the poly(quaternary ammonium) polymers prepared and disclosed in French Patent 2,270,846, the disclosure of which is incorporated by reference herein, which are composed of repeating units corresponding to the following formula (IV):

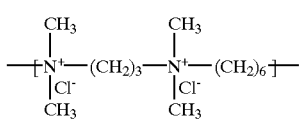

(IV)

the weight-average molar mass of which, determined by gel permeation chromatography, ranges from 9500 to 9900; and the poly(quaternary ammonium) polymers prepared and disclosed in French Patent 2,270,846, the disclosure of which is incorporated by reference herein, which are composed of repeat units corresponding to the following formula (V):

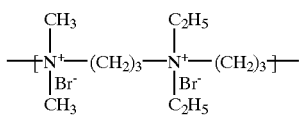

(V)

the weight-average molar mass of which, determined by gel permeation chromatography, is approximately 1200.

The medium of the composition (A) which is appropriate for dyeing is preferably an aqueous medium composed predominantly of water and optionally comprising cosmetically acceptable organic solvents, such as alcohols, for example ethyl alcohol, isopropyl alcohol, benzyl alcohol and phenylethyl alcohol, and glycols or glycol ethers, such as ethylene glycol monomethyl, monoethyl and monobutyl ethers, propylene glycol or its ethers, such as propylene glycol monomethyl ether, butylene glycol, and dipropylene glycol and the alkyl ethers of diethylene glycol, such as, for example, diethylene glycol monomethyl or monobutyl ether. When organic solvents are present, they are preferably used in concentrations ranging from approximately 0.5 to 20% by weight, preferably from approximately 2 to 10% by weight, with respect to the total weight of the composition.

The composition (A) can also comprise an effective amount of other agents commonly used in the field of oxidation dyeing. These adjuvants can include, for example, sequestering agents, hair conditioning agents, in particular silicones, preserving agents, opacifying agents, and the like, and anionic, nonionic or amphoteric surface-active agents or their mixtures.

Of course, a person skilled in the art will take care to choose the optional additional compound or compounds mentioned above so that the advantageous properties intrinsically attached to the dyeing composition according to the invention are not, or virtually not, detrimentally affected by the envisaged addition or additions.

The values of the pH of the compositions (A) and (B) can be chosen in particular so that the value of the pH of the ready-for-use composition, resulting from the mixing of the dyeing composition (A) and of the oxidizing composition (B), generally ranges from 3 to 11, preferably from 4 to 9, and more preferably from 6 to 8. They can be adjusted by means of acidifying or basifying agents well known in the art of the oxidation dyeing of keratinous fibers.

Mention may be made, among basifying agents, of, for example, ammonia, alkaline carbonates, alkanolamines, such as mono-, di- and triethanolamines and their derivatives, sodium hydroxide, potassium hydroxide and the compounds of the following formula (VI):

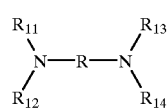

(VI)

in which R is a propylene residue optionally substituted by a hydroxyl group or a $C_{1-4}$ alkyl radical, and $R_{11}$, $R_{12}$, $R_{13}$ and $R_{14}$, which are identical or different, represent a hydrogen atom or a $C_{1-4}$ alkyl or $C_{1-4}$ hydroxyalkyl radical.

The acidifying agents are conventionally, by way of example, inorganic or organic acids, such as hydrochloric acid, orthophosphoric acid, carboxylic acids, such as tartaric acid, citric acid or lactic acid, or sulphonic acids.

Another subject of the present invention is a ready-for-use composition for the dyeing of keratinous fibers comprising the laccase and the oxidation dye and at least one ketose, or which is capable of being obtained by mixing the compositions (A) and (B) defined above.

Another subject of the invention is a process for dyeing keratinous fibers and in particular human keratinous fibers, such as the hair, employing the dyeing compositions as defined above.

According to this process, at least one ready-for-use dyeing composition as defined above is applied to the fibers for a time sufficient to develop the desired coloring, after which the hair is rinsed, optionally washed with shampoo, rinsed again and dried.

The time necessary for the development of the coloring on the keratinous fibers generally ranges from 3 to 60 minutes, and more specifically from 5 to 40 minutes.

The application of the ready-for-use dyeing composition can take place in particular at a temperature ranging from room temperature (20° C.) to 60° C., and preferably from 35 to 50° C.

According to a specific embodiment of the invention, the process comprises a preliminary stage which comprises separately storing, on the one hand, a composition (A) as defined above and, on the other hand, a composition (B) defined above, and then mixing them at the time of use before applying this mixture to the keratinous fibers.

Another subject of the invention is dyeing multi-compartment devices or dyeing kits comprising at least two compartments, one of which contains a composition (A) comprising at least one oxidation dye and a ketose in an amount ranging from 0.1 to 15% by weight of the total weight of the composition (A), and another of which contains an oxidizing composition (B) comprising at least one laccase. These devices can be equipped with a means, such as the devices disclosed in Patent FR-2,586,913, the disclosure of which is incorporated by reference herein, which allows the desired mixture to be delivered to the hair.

It is clearly understood that the description which precedes has only been given purely by way of illustration and without implied limitation and that alternative forms or modifications can be introduced thereto within the scope of the present invention.

Concrete examples illustrating the invention will now be given without, however, limiting its scope.

COMPARATIVE EXAMPLES

The following dyeing compositions were prepared (contents in grams):

| EXAMPLE | 1* | 2* | 3 | 4 | 5* |
|---|---|---|---|---|---|
| para-Phenylenediamine ($10^{-3}$ mol) | 0.108 g | 0.108 g | 0.108 g | 0.108 g | 0.108 g |
| 1-Methyl-2-hydroxy-4-aminobenzene ($10^{-3}$ mol) | 0.123 g | 0.123 g | 0.123 g | 0.123 g | 0.123 g |
| Fructose | — | — | 5 g | 10 g | — |
| Glucose | — | 5 g | — | — | — |
| Erythorbic acid | — | — | — | — | 0.3 g |
| Phosphate buffer, sold under the name TITRISOL by the company Merck | pH 7 | pH 7 | pH 7 | pH 7 | pH 7 |
| Demineralized water, q.s. for | (100 − x) g | (100 − x) g | (100 − x) g | (100 − x) g | (100 − x) g |

*Examples not forming part of the invention

At the time of use, x g of a laccase solution were added in order to obtain a final dyeing composition having a laccase concentration equal to $10^7$ u units.

Then, each of the dyeing compositions obtained was applied to locks of natural grey hair comprising 90% white hairs, at a proportion of 5 g of composition per g of hair, for 30 minutes at 40° C. The hair was subsequently rinsed, washed with shampoo, rinsed again and then dried.

The hair dyed with the compositions 1*, 2*, 3, 4 and 5* exhibit the same shade (medium red purple).

In order to more precisely determine the absorption of the coloring, the color of the locks was evaluated before and after dyeing in the Munsell system by means of a Minolta CM-2002® colorimeter.

According to the Munsell notation, a color is defined by the expression H V/C, in which the three parameters respectively denote the tint or Hue (H), the intensity or Value (V) and the purity or Chromaticity (C); the oblique stroke in this expression is simply a convention and does not indicate a ratio.

The difference between the color of the lock before dyeing and the color of the lock after dyeing expresses the intensity of the coloring and was calculated by applying the Nickerson formula:

$$\Delta E = 0.4 C_0 \Delta H + 6 \Delta V + 3 \Delta C$$

as described, for example, in "Couleur, Industrie et Technique" (Color, Industry and Technology), pages 14–17, Vol. No. 5, 1978, the disclosure of which is incorporated by reference herein.

In this formula, $\Delta E$ represents the difference in color between two locks, $\Delta H$, $\Delta V$ and $\Delta C$ represent the variation in absolute value of the parameters H, V and C, and $C_0$ represents the purity of the lock with respect to which it is desired to evaluate the difference in color.

The higher the value of $\Delta E$, the more intense the coloring.

The results are given in the table hereinbelow:

| Composition | $\Delta E$ |
|---|---|
| 1 (*) | 30.94 |
| 2 (*) | 31.29 |
| 3 | 32.65 |
| 4 | 32.39 |
| 5 (*) | 5.75 |

These results show that the composition 2*, which does not form part of the invention, and the compositions 3 and 4, which are in accordance with the invention, result in a coloring which is as intense as that of the composition 1*, which does not form part of the invention and which does not comprise a reducing agent. On the other hand, the coloring obtained with the composition 5*, which does not form part of the invention and which uses erythorbic acid as reducing agent, is weak. Thus, the use of ketose does not slow down the absorption of the coloring and makes it possible to obtain colorings which are as intense as those obtained without a reducing agent.

The dyeing compositions 2*, 3 and 4 mentioned hereinabove were also stored at a room temperature of 22° C.±2° C. for 2 weeks.

The same colorings as those described above were subsequently produced.

The results are given in the following table:

| Composition | $\Delta E$ |
|---|---|
| 2(*) | 13.58 |
| 3 | 31.97 |
| 4 | 30.89 |

Thus, only the use of a ketose as reducing agent makes it possible to reduce oxidation of the coloring precursors by not modifying, over time, the absorption of the coloring on the fibers.

What is claimed is:
1. A composition for dyeing of keratinous fibers comprising, in a medium appropriate for dyeing:
   a ketose as reducing agent, wherein said ketose is present in an amount ranging from 0.1 to 15% by weight with respect to the total weight of the composition, at least one laccase as oxidizing agent, and
at least one oxidation dye.

2. A composition according to claim 1, wherein said keratinous fibers are human keratinous fibers.

3. A composition according to claim 2, wherein said human keratinous fibers are hair.

4. A composition according to claim 1, wherein said at least one oxidation dye comprises an oxidation dye precursor.

5. A composition according to claim 4, wherein said at least one oxidation dye further comprises at least one coupler.

6. A composition according to claim 1, wherein said at least one oxidation dye comprises a coupler or a combination of couplers.

7. A composition according to claim 1, wherein said ketose is chosen from ketohexoses.

8. A composition according to claim 7, wherein said ketose is fructose.

9. A composition according to claim 1, wherein said ketose is present in an amount ranging from 5 to 10% by weight with respect to the total weight of the composition.

10. A composition according to claim 1, wherein said at least one laccase is chosen from laccases of plant origin, animal origin, fungal origin, and bacterial origin, or wherein said laccase is obtained by biotechnology.

11. A composition according to claim 10, wherein said at least one laccase is chosen from laccases produced by plants carrying out chlorophyll synthesis.

12. A composition according to claim 11, wherein said at least one laccase is chosen from those extracted from the Anacardiaceae, the Podocarpaceae, Rosmarinus off., *Solanum tuberosum*, Iris sp., Coffea sp., *Daucus carrota, Vinca minor, Persea americana, Catharenthus roseus*, Musa sp., *Malus pumila, Gingko biloba, Monotropa hypopithys,* Aesculus sp., *Acer pseudoplatanus, Prunus persica* and *Pistacia palaestina*.

13. A composition according to claim 10, wherein said at least one laccase is chosen from laccases resulting from *Pyricularia orizae, Polyporus versicolor, Rhizoctonia praticola, Rhus vernicifera*, Scytalidium, *Polyporus pinsitus, Myceliophtora thermophila, Rhizoctonia solani, Tramates versicolor, Fomes fomentarius, Chaetomium thermophile, Neurospora crassa, Coriolus versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune*, and *Dichomitius squalens*.

14. A composition according to claim 1, wherein said at least one laccase is present in an amount ranging from 0.5 to 3000 lacu, from 1000 to 6×10$^7$ u units, or from 20 to 3×10$^6$ ulac units per 100 g of said composition.

15. A composition according to claim 4, wherein said oxidation dye precursor is chosen from ortho- or para-phenylenediamines, bisphenylalkylenediamines, ortho- or para-aminophenols, heterocyclic bases and acid addition salts thereof.

16. A composition according to claim 4, wherein said oxidation dye precursor is present in an amount ranging from 0.0005 to 12% by weight with respect to the total weight of the composition.

17. A composition according to claim 5, wherein said at least one coupler is chosen from meta-phenylenediamines, meta-aminophenols, meta-diphenols, heterocyclic couplers and acid addition salts thereof.

18. A composition according to claim 17, wherein said at least one coupler is present in an amount ranging from 0.0001 to 10% by weight with respect to the total weight of the composition.

19. A composition according to claim 6, wherein said couplers are chosen from meta-phenylenediamines, meta-aminophenols, meta-diphenols, heterocyclic couplers and acid addition salts thereof.

20. A composition according to claim 19, wherein said couplers are present in an amount ranging from 0.0001 to 10% by weight with respect to the total weight of the composition.

21. A composition according to claim 15, wherein said acid addition salts are chosen from hydrochlorides, hydrobromides, sulphates, tartrates, lactates, and acetates.

22. A composition according to claim 17, wherein said acid addition salts are chosen from hydrochlorides, hydrobromides, sulphates, tartrates, lactates, and acetates.

23. A composition according to claim 1, wherein said composition additionally comprises at least one direct dye.

24. A composition according to claim 1, wherein said composition additionally comprises at least one amphoteric or cationic substantive polymer.

25. A composition according to claim 24, wherein said substantive polymer is a poly(quatemary ammonium) polymer comprising repeating units of formula (IV):

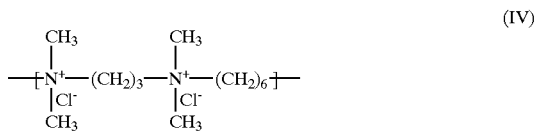

(IV)

26. A composition according to claim 24, wherein said substantive polymer is a poly(quaternary ammonium) polymer comprising repeating units of formula (V):

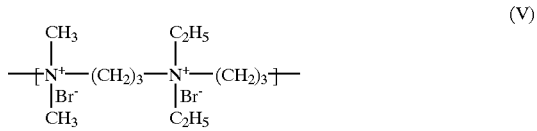

(V)

27. A composition according to claim 1, wherein said composition additionally comprises at least one adjuvant chosen from sequestering agents, hair conditioning agents, preserving agents, opacifying agents, anionic, nonionic or amphoteric surface-active agents, and mixtures thereof.

28. A composition according to claim 27, wherein said hair conditioning agents are silicones.

29. A composition according to claim 1, wherein said composition has a pH ranging from 3 to 11.

30. A composition according to claim 29, wherein said composition has a pH ranging from 4 to 9.

31. A composition according to claim 30, wherein said composition has a pH ranging from 6 to 8.

32. A process for dyeing keratinous fibers comprising:
applying to said fibers a dyeing composition comprising, in a medium appropriate for dyeing, at least one oxidation dye, and a ketose as reducing agent, wherein said ketose is present in an amount ranging from 0.1 to 15% by weight with respect to the total weight of said dyeing composition, and
developing the color, in the presence of air, in an alkaline, neutral or acidic medium, using at least one laccase, wherein said at least one laccase is contained in said dyeing composition or in a separate oxidizing composition.

33. A process according to claim 32, wherein said at least one laccase is contained in a separate oxidizing composition, and wherein said dyeing and oxidizing compositions are mixed immediately before use or applied sequentially one after the other to said keratinous fibers.

34. A process according to claim 32, wherein said keratinous fibers are human keratinous fibers.

35. A process according to claim 34, wherein said human keratinous fibers are hair.

36. A process according to claim 32, wherein said at least one oxidation dye comprises an oxidation dye precursor.

37. A process according to claim 36, wherein said at least one oxidation dye further comprises at least one coupler.

38. A process according to claim 32, wherein said at least one oxidation dye comprises a coupler or a combination of couplers.

39. A process according to claim 32, wherein said ketose is chosen from ketohexoses.

40. A process according to claim 39, wherein said ketose is fructose.

41. A process according to claim 32, wherein said ketose is present in an amount ranging from 5 to 10% by weight with respect to the total weight of said dyeing composition.

42. A process according to claim 32, wherein said at least one laccase is chosen from laccases of plant origin, animal origin, fungal origin, and bacterial origin, or wherein said laccase is obtained by biotechnology.

43. A process according to claim 42, wherein said at least one laccase is chosen from laccases produced by plants carrying out chlorophyll synthesis.

44. A process according to claim 43, wherein said laccase is chosen from laccases extracted from the Anacardiaceae, the Podocarpaceae, Rosmarinus off., *Solanum tuberosum*, Iris sp., *Coffea* sp., *Daucus carrota*, *Vinca minor*, *Persea americana*, *Catharenthus roseus*, Musa sp., *Malus pumila*, *Gingko biloba*, *Monotropa hypopithys*, Aesculus sp., *Acer pseudoplatanus*, *Prunus persica*, and *Pistacia palaestina*.

45. A process according to claim 42, wherein said at least one laccase is chosen from laccases resulting from *Pyricularia orizae*, *Polyporus versicolor*, *Rhizoctonia praticola*, *Rhus vernicifera*, Scytalidium, *Polyporus pinsitus*, *Myceliophtora thermophila*, *Rhizoctonia solani*, *Tramates versicolor*, *Fomes fomentarius*, *Chaetomium thermophile*, *Neurospora crassa*, *Coriolus versicol*, *Botrytis cinerea*, *Rigidoporus lignosus*, *Phellinus noxius*, *Pleurotus ostreatus*, *Aspergillus nidulans*, *Podospora anserina*, *Agaricus bisporus*, *Ganoderma lucidum*, *Glomerella cingulata*, *Lactarius piperatus*, *Russula delica*, *Heterobasidion annosum*, *Thelephora terrestris*, *Cladosporium cladosporioides*, *Cerrena unicolor*, *Coriolus hirsutus*, *Ceriporiopsis subvermispora*, *Coprinus cinereus*, *Panaeolus papilionaceus*, *Panaeolus sphinctrinus*, *Schizophyllum commune*, and *Dichomitius squalens*.

46. A process according to claim 32, wherein said at least one laccase is present in an amount ranging from 0.5 to 3000 lacu, from 1000 to $6 \times 10^7$ u units, or from 20 to $3 \times 10^6$ ulac units per 100 g of said dyeing composition when said at least one laccase is contained in said dyeing composition, or per 100 g of the combination of said dyeing composition and said oxidizing composition when said at least one laccase is contained in said oxidizing composition.

47. A process according to claim 36, wherein said oxidation dye precursor is chosen from ortho- or para-phenylenediamines, bisphenylalkylenediamines, ortho- or para-aminophenols, heterocyclic bases and acid addition salts thereof.

48. A process according to claim 36, wherein said oxidation dye precursor is present in an amount ranging from 0.0005 to 12% by weight with respect to the total weight of the dyeing composition.

49. A process according to claim 37, wherein said at least one coupler is chosen from meta-phenylenediamines, meta-aminophenols, meta-diphenols, heterocyclic couplers, and acid addition salts thereof.

50. A process according to claim 49, wherein said at least one coupler is present in an amount ranging from 0.0001 to 10% by weight with respect to the total weight of the dyeing composition.

51. A process according to claim 38, wherein said couplers are chosen from meta-phenylenediamines, meta-aminophenols, meta-diphenols, heterocyclic couplers, and acid addition salts thereof.

52. A process according to claim 51, wherein said couplers are present in an amount ranging from 0.0001 to 10% by weight with respect to the total weight of the dyeing composition.

53. A process according to claim 47, wherein said acid addition salts are chosen from hydrochlorides, hydrobromides, sulphates, tartrates, lactates and acetates.

54. A process according to claim 49, wherein said acid addition salts are chosen from hydrochlorides, hydrobromides, sulphates, tartrates, lactates and acetates.

55. A process according to claim 32, wherein said dyeing composition additionally comprises at least one direct dye.

56. A process according to claim 32, wherein said dyeing composition and/or said oxidizing composition additionally comprises at least one amphoteric or cationic substantive polymer.

57. A process according to claim 56, wherein said substantive polymer is a poly(quaternary ammonium) polymer comprising repeating units of formula (IV):

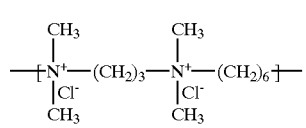

(IV)

58. A process according to claim 56, wherein said substantive polymer is a poly(quaternary ammonium) polymer comprising repeating units of formula (V):

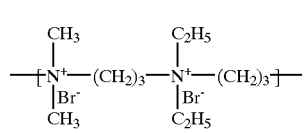

(V)

59. A process according to claim 32, wherein said composition (A) additionally comprises at least one adjuvant chosen from sequestering agents, hair conditioning agents, preserving agents, opacifying agents, anionic, nonionic or amphoteric surface-active agents, and mixtures thereof.

60. A process according to claim 59, wherein said hair conditioning agents are silicones.

61. A process according to claim 32, wherein the pH of said dyeing composition ranges from 3 to 11 when said at least one laccase is contained in said dyeing composition, or wherein the pH of the combination of said dyeing composition and said oxidizing composition ranges from 3 to 11 when said at least one laccase is contained in said oxidizing composition.

62. A process according to claim 61, wherein said pH ranges from 4 to 9.

63. A process according to claim 62, wherein said pH ranges from 6 to 8.

64. A process for dyeing keratinous fibers, comprising applying at least one dyeing composition to said fibers for a time sufficient to develop the desired coloring, wherein said dyeing composition comprises, in a medium appropriate for dyeing, a ketose as reducing agent, wherein said ketose is present in an amount ranging from 0.1 to 15% by weight with respect to the total weight of the composition, at least one laccase as oxidizing agent, and at least one oxidation dye.

65. A process for dyeing keratinous fibers, comprising applying a ready-for-use composition to said fibers for a time sufficient to develop the desired coloring, wherein said ready-for-use composition is obtained by mixing:

a dyeing composition comprising, in a medium appropriate for dyeing, at least one oxidation dye, and a ketose as reducing agent, wherein said ketose is present in an amount ranging from 0.1 to 15% by weight with respect to the total weight of said dyeing composition, and an oxidizing composition comprising at least one laccase.

66. A process according to claim 65, further comprising separately storing said dyeing composition and said oxidizing composition, and mixing said dyeing composition and said oxidizing composition at the time of use before applying the mixture to said keratinous fibers.

67. A process according to claim 65, wherein the application of said ready-for-use composition to said keratinous fibers is carried out at a temperature ranging from 20 to 60° C.

68. A process according to claim 67, wherein said temperature ranges from 35 to 50° C.

69. A multi-compartment kit for the dyeing of keratinous fibers, comprising at least two compartments, wherein one of the compartments contains a dyeing composition comprising at least one oxidation dye and at least one ketose, wherein said ketose is present in an amount ranging from 0.1 to 15% by weight with respect to the total weight of the dyeing composition, and another compartment contains an oxidizing composition comprising at least one laccase.

* * * * *